United States Patent
Hirasawa et al.

(10) Patent No.: US 7,169,579 B2
(45) Date of Patent: Jan. 30, 2007

(54) **METHOD OF ISOLATING *STREPTOCOCCUS SOBRINUS* AND SELECTION MEDIUM**

(75) Inventors: Masatomo Hirasawa, Tokyo (JP); Kazuko Takada, Tokyo (JP)

(73) Assignee: Nihon University, Tokyo (JP)

( * ) Notice: Subject to any disclaimer, the term of this patent is extended or adjusted under 35 U.S.C. 154(b) by 314 days.

(21) Appl. No.: 10/484,426

(22) PCT Filed: Jul. 4, 2002

(86) PCT No.: PCT/JP02/06822

§ 371 (c)(1),
(2), (4) Date: May 13, 2004

(87) PCT Pub. No.: WO03/012073

PCT Pub. Date: Feb. 13, 2003

(65) Prior Publication Data

US 2004/0185523 A1 Sep. 23, 2004

(30) Foreign Application Priority Data

Jul. 27, 2001 (JP) .............................. 2001-227137

(51) Int. Cl.
*C12Q 1/04* (2006.01)
(52) U.S. Cl. .......................................... 435/34; 435/36
(58) Field of Classification Search ................ 435/34, 435/36, 253.4, 885
See application file for complete search history.

(56) References Cited

U.S. PATENT DOCUMENTS 5,374,538 A * 12/1994 Bratthall ...................... 435/36

FOREIGN PATENT DOCUMENTS

| JP | 11-069970 | 3/1999 |
| JP | 2002-27975 | 1/2002 |
| JP | 2002-105100 | 4/2002 |

OTHER PUBLICATIONS

Luengpailin J. et al. Glycine Prevents the Phenotypic Expression of *Streptococcal* Glucan Binding Lectin. Biochimica et Biophysica Acta 1474(2)212-218, Apr. 2000.*
Hirasawa M. et al. Susceptibility of *S. mutans* and *S. sobrinus* to Cell Wall inhibitors . . . Caries Research 36(3)155-160, May-Jun. 2002.*
Hirasawa M, et al. "Susceptibility of *Streptococcus mutans* and *Streptococcus sobrinus* to cell wall Inhibitors and development of a novel selective medium for *S. sobrinus*". Caries Res, vol. 36, No. 3, pp. 155-160 05-06/02 May 2002.
Luengpailin J. et al. "Glycine prevents phenotypic expression of *Streptococcal* glucan-binding lectin". Biochem, vol. 1474, No. 2, pp. 212-218, Apr. 2000.

* cited by examiner

*Primary Examiner*—Ralph Gitomer
(74) *Attorney, Agent, or Firm*—Oblon, Spivak, McClelland, Maier & Neustadt, P.C.

(57) ABSTRACT

A method of selectively isolating *Streptococcus sobrinus* alone out of oral streptococci including mutans streptococci, and a medium for selecting *Streptococcus sobrinus* are developed.

A method of substantially isolating *Streptococcus sobrinus* alone by the addition of a monobactam antibiotic to a medium on which only oral streptococci including mutans streptococci can grow; and a selective medium for *Streptococcus sobrinus* prepared by the addition of a monobactam antibiotic to a medium on which only oral streptococci including mutans streptococci can grow, are provided with.

16 Claims, No Drawings

METHOD OF ISOLATING *STREPTOCOCCUS SOBRINUS* AND SELECTION MEDIUM

This application is a National Stage Application filed under Rule 371 based on PCT/JP02/06822 filed Jul. 4, 2002, which claims priority to Application Japan 2001 227137 filed Jul. 27, 2001.

TECHNICAL FIELD

The present invention relates to a method of selectively isolating *Streptococcus sobrinus* out of dental caries-causing bacteria (mutans streptococci) inhabiting in the oral cavity, and a medium which allows *Streptococcus sobrinus* alone to selectively grow.

BACKGROUND ART

Heretofore, it has been said that the bacteria which cause dental caries in human is *Streptococcus mutans* out of streptococci (oral streptococci) inhabiting in the oral cavity. However, it is considered nowadays that dental caries is caused by a group of bacteria generically called as mutans streptococci which is constituted by bacterial species distinguished from each other in the different serotypes a to h (Hamada, S. and H. D. Slade, 1980, Microbiological Review 44:331–384; Hirasawa, M. et al., 1980, Infect. Immun. 27:1003–1011; and Loesche, W. J., 1986, Microbiological Review 50:353–380). Oral streptococci classified into mutans streptococci include *Streptococcus cricetus, Streptococcus rattus, Streptococcus mutans, Streptococcus sobrinus* and *Streptococcus downeii*.

Further, the recognition is recently being accepted that *Streptococcus mutans* and *Streptococcus sobrinus* out of the bacteria classified into mutans streptococci play particularly important roles in dental caries. Particularly, in Europe, the significance of *Streptococcus sobrinus* attracts attention, and there are reports that caries risk in the case where both of *Streptococcus mutans* and *Streptococcus sobrinus* inhabit in the oral cavity becomes higher than that in the case of *Streptococcus mutans* alone (Babaahmady, K. G. et al., 1998, Caries Res. 32:51–58; Kohler, B. and S. Bjarnason, 1987, Community Dent. Oral Epidemiol. 15:332–335; and Lindquist, S. and C. G. Emilson, 1991, Caries Res. 25:146–152). However, the distribution of *Streptococcus mutans* and *Streptococcus sobrinus* in dental caries, and the relative significance thereof to dental caries have not been clarified.

In Japan, it has been said that mainly found out the clinical samples of dental caries (carious cavity, dental plaque and saliva) is *Streptococcus mutans*. However, it is now discussed by the researchers how many *Streptococcus sobrinus* inhabit the oral cavity, and, whether or not the presence of *Streptococcus sobrinus* is really important for caries risk.

Mitis Salivarius Agar (MS, manufactured by Difco) is conventionally used as a selective medium for streptococci in the oral cavity. A medium prepared by the addition of sucrose and an antibiotic bacitracin to the Mitis Salivarius Agar is used as a selective medium for mutans streptococci (MSB medium). However, it is known that in the MSB medium, the recovery of *Streptococcus sobrinus* is lower than that of *Streptococcus mutans*. Further, *Streptococcus mutans* and *Streptococcus sobrinus* are closely resemble to each other in their colony morphology and so on, therefore, unless a researcher is conversant with the colony morphology of these species, under the circumstances, he or she cannot distinguish these species inhabiting on the same plate medium from each other by observation with the naked eye.

Some methods for detection and identification of *Streptococcus mutans* and *Streptococcus sobrinus* individually were reported. In these methods, these two kinds of bacteria are separated out of the oral streptococci including these two kinds of bacteria by means of a selective medium capable of substantially selecting these two kinds of bacteria alone, followed by biochemical or serological tests to distinguish these two species from each other (Gold, O. G. et al., 1973, Archs. Oral Biol. 18:1357–1364; Hirasawa, M. et al., 1980, Infect. Immun. 27:697–699; Kimmel, L. and N. Tinanoff, 1991, Oral Microbiol. Immunol. 6:275–279; Linke, H. A. B., 1977, J. Clin. Microbiol. 5:604–609; Schaeken, M. J. M. et al., 1986, J. Dent. Res. 65:906–908; Takada, K. et al., 1984, Infect. Immun. 45:464–469; and Wada, W. G. et al., 1986, J. Med. Microbiol. 22:319–323), or by a DNA prove method to distinguish them (Igarashi, T. et al., 1996, Oral Microbiol. Immunol. 5:294–298; and Shiroza, T. et al., 1998, Oral Microbiol. Immunol. 13:11–16). Further, some selective media for *Streptococcus mutans* have been reported (Gold, O. G. et al., 1973, Archs. Oral Biol. 18:1357–1364; Kimmel, L. and N. Tinanoff, 1991, Oral Microbiol. Immunol. 6:275–279; Linke, H. A. B., 1977, J. Clin. Microbiol. 5:604–609; Schaeken, M. J. M. et al., 1986, J. Dent. Res. 65:906–908; and Wada, W. G. et al., 1986, J. Med. Microbiol. 22:319–323). However, up to the present date, no selective culture technique capable of isolating *Streptococcus sobrinus* alone has been reported. Furthermore, the difference in the susceptibility to antibiotics between the different serotypes of mutans streptococci has been reported (Little, W. A. et al., 1979, Antimicrob. Agents Chemother. 15:440–443). However, no antibiotic which has the possibility to select *Streptococcus sobrinus* alone has not yet found.

DISCLOSURE OF THE INVENTION

The object of the present invention is to develop a method of selectively isolating *Streptococcus sobrinus* alone out of the population of oral streptococci including mutans streptococci, and a selective medium for selecting *Streptococcus sobrinus*.

In order to attain the above-mentioned object, the present inventors focused the susceptibilities of mutans streptococci to cell wall inhibitors, and tested the susceptibilities thereof to various types of antibiotics. As the results, the difference between *Streptococcus mutans* and *Streptococcus sobrinus* in their susceptibility to monobactam antibiotics was found, and the present invention was accomplished by the finding.

Namely, the present invention is to provide a method of substantially isolating *Streptococcus sobrinus* alone by the addition of a monobactam antibiotic to a medium on which oral streptococci including mutans streptococci can grow, and a selective medium for *Streptococcus sobrinus* prepared by the addition of a monobactam antibiotic to a medium on which oral streptococci including mutans streptococci can grow.

In the present invention, it is preferred that the medium on which only the oral streptococci can grow is Mitis Salivarius Agar (MS medium; manufactured by Difco).

In the present invention, as the monobactam antibiotic, aztreonam (AZT) or carumonam (CRMN) is preferred, and aztreonam (AZT) is particularly preferred. Here, the monobactam antibiotic is preferably added in a concentration of from 0.05 to 0.5 g/L.

The selective medium for *Streptococcus sobrinus* of the present invention preferably contains fosfomycin and/or bacitracin.

Further, it is particularly preferred that the selective medium for *Streptococcus sobrinus* of the present invention has the following composition:

| | |
|---|---|
| Mitis Salivarius Medium | 90 g/L |
| Aztreonam | 0.05–0.5 g/L |
| Fosfomycin | 0.05–0.5 g/L |
| Bacitracin | 5–50 units/L |
| Sodium Chloride | 5–40 g/L |

BEST MODE FOR CARRYING OUT THE INVENTION

The method and selective medium of the present invention are characterized in that a monobactam antibiotic is added to a medium on which oral streptococci including mutans streptococci can grow.

In the background of the present invention, there is the fact that distinction of *Streptococcus mutans* and *Streptococcus sobrinus* on the medium on which the two kinds of bacteria inhabit together requires a lot of skill, since the two kinds of bacteria which attract the researchers attention as the major dental caries-causing bacteria among oral streptococci classified into the mutans streptococci, are extremely resemble to each other in their colony morphology and so on as is mentioned above. Here, mutans streptococci other than *Streptococcus mutans* and *Streptococcus sobrinus* have respective identifiable features in their colony morphologies and so on without requiring the particular skin, therefore, even if these bacteria inhabit together with *Streptococcus mutans* or *Streptococcus sobrinus* on the same medium, these two kinds of bacteria can easily be differentiated from the other bacteria.

In view of the above-mentioned background, in the present invention, the present inventors narrowed the focus to clearly differentiate *Streptococcus mutans* and *Streptococcus sobrinus*, searched for antibiotics to which significant difference between the two kinds of bacteria in their susceptibilities was observed, and prepared a selective medium for *Streptococcus sobrinus*, on which *Streptococcus sobrinus* alone could substantially grow.

Now, test conditions such as materials and methods used in the tests carried out in the research to accomplish the present invention will be described.

<Materials and Methods>

Bacterial Strains

All of the bacterial strains used in the research are shown in Table 1 described below.

TABLE 1

| Strain | Serotype |
|---|---|
| <Mutans streptococci> | |
| *Streptococcus cricetus* | |
| OMZ-61 | a |
| E49 | a |
| *Streptococcus rattus* | |
| BHT | b |
| FA1 | b |

TABLE 1-continued

| Strain | Serotype |
|---|---|
| *Streptococcus mutans* | |
| PS14 | c |
| Ingbritt | c |
| JC2 | c |
| NCTC10449 | c |
| LM7 | e |
| NUM-Sme1 | e |
| OMZ175 | f |
| NUM-Smf1 | f |
| *Streptococcus sobrinus* | |
| OMZ176 | d |
| B13 | d |
| NUM-Ssd1 | d |
| NUM-Ssd2 | d |
| NIDR6715 | g |
| OMZ65 | g |
| NUM-Ssg1 | g |
| *Streptococcus downeii* | |
| NCTC11391 | h |
| <Oral Streptococci> | |
| *Streptococcus salivarius* | |
| ATCC9222 | |
| HHT | |
| *Streptococcus mitis* | |
| NCTC3168 | |
| ATCC903 | |
| *Streptococcus sanguis* | |
| ATCC10556 | |
| *Streptococcus oralis* | |
| ATCC10557 | |
| *Streptococcus gordonii* | |
| ATCC10558 | |
| Challis | |
| *Streptococcus anginosus* | |
| ATCC9895 | |
| NCTC10709 | |

Out of the above-described bacterial strains, the strains indicated by NUM-Sme, NUM-Smf, NUM-Ssd and NUM-Ssg were strains isolated from clinical samples, and identified by the combination of a colony morphological method and a serological method (Hamada, S. and H. D. Slade, 1980, Microbiological Review 44:331–384; Hirasawa, M. et al., 1980, Infect. Immun. 27:697–699; and Takada, K. et al., 1984, Infect. Immun. 45:464–469).

Out of the other bacterial strains, the strains to which "ATCC" is attached were purchased from American type Culture Correction, the strains to which "NCTC" is attached were purchased from National Collection Type Culture, and the other strains are those which have been preserved before in the laboratory to which the present inventors belong.

All the bacterial strains were grown and maintained anaerobically at 37° C. on Brain Heart Infusion (BHI broth, manufactured by Difco Laboratories, Detroit, Mich.) agar plates supplemented with 5% (v/v) horse blood.

Susceptibility Test to Antibiotics

The susceptibility test was carried out in accordance with microbroth dilution method.

In order to develop a selective medium for *Streptococcus sobrinus*, the preliminary study for selection of antibiotics was carried out by a disk susceptibility test (Sensi-Disc;

manufactured by Becton Dickinson Co., USA) (no data given herein), and on the basis of the result of the preliminary study, the antibiotics used in the main test were determined. The antibiotics used in the main test were described below.

Cephaloridine (manufactured by Sigma Chemical Co., MO. USA)

Cefazoline (manufactured by Wako Pure Chemical Industries Ltd., Tokyo, Japan)

Cloxacillin (manufactured by Sigma)

Imipenem (manufactured by Banyu Pharmaceutical Co., Ltd., Tokyo, Japan)

Aztreonam (AZT) (manufactured by ICN Biomedicals Inc., OH, USA)

Carumonam (CAM) (manufactured by Takeda Chemical Industries Ltd., Osaka, Japan)

Cephalexin (manufactured by Sigma)

Benzylpenicillin (Wako Pure Chemical Industries Ltd.)

Cefoxitin (manufactured by Sigma)

The above-described antibiotics were dissolved in an appropriate solution, respectively, and the respective antibiotic solutions were divided into serial two-fold dilutions in a 96-well microtiter plates containing BHI broth. The bacteria were precultured in BHI broth, respectively, and inoculated into the wells containing the antibiotic solution to make a final concentration of the bacteria to be $1 \times 10^4$ cells/well, respectively. The plates were anaerobically incubated at a temperature of 37° C. for 48 hours. After mixing the broth in each well by the use of a pipette, the absorbance at 550 nm in each well was measured with a microplate reader (manufactured by Corona Electric Co., Ibaraki, Japan), to determine bacterial growth. The antibiotic concentration at which no bacterial growth was observed was defined as the minimal inhibitory concentration (MIC).

Aliquots of 10 µl of the broth in the well, which no bacterial growth was observed were inoculated onto Mitis Salivarius Agar (MS medium; manufactured by Difco) plates, respectively, and anaerobically incubated at a temperature of 37° C. for 48 hours. The recovery of the inoculated bacteria was calculated to estimate which the mechanism of growth inhibition was bactericidal or bacteriostatic.

Results

Results of the susceptibility tests of *Streptococcus mutans* and *Streptococcus sobrinus* to β-lactam antibiotics are shown in Table 2 below.

From the results shown in Table 2, as to cepharoridine, cefazoline and cephalexin, no significant difference between *Streptococcus mutans* and *Streptococcus sobrinus* in their susceptibilities were observed.

As to cloxacillin, the susceptibilities of *Streptococcus mutans* were twice as high.

As to imipenem, the susceptibilities of *Streptococcus sobrinus* were approximately from 4 to 8 times as high as those of *Streptococcus mutans*.

As to benzylpenicillin, contrary to cloxacillin, the susceptibilities of *Streptococcus sobrinus* were twice as high.

As to cefoxitin, although only OMZ176 strain out of *Streptococcus sobrinus* indicated the susceptibility thereto approximately 4 times as high as those of the other bacterial strains, no significant difference between *Streptococcus mutans* and *Streptococcus sobrinus* in their susceptibilities was observed.

As to aztreonam and carumonam classified into monobactam antibiotics, the MICs of the both antibiotics to *Streptococcus mutans* were 125 µg/mL, respectively, while the MICs of these antibiotics to *Streptococcus sobrinus* were 2000 µg/mL, respectively, it becoming clear that the susceptibilities of *Streptococcus mutans* to these antibiotics were 16-fold as high as those of *Streptococcus sobrinus*. These observations indicate that the monobactam antibiotics are useful agents for separation of *Streptococcus sobrinus* from *Streptococcus mutans*.

It has been reported that imipenem, aztreonam and carumonam targeted the penicillin-binding protein-3 (PBP-3) with respect to *E. coli* (Georgopapadakou, N. H. et al., 1982, Antimicrob. Agents Chemother. 21:950–956; and Imada, A. et al., 1985, Antimicrob. Agents Chemother. 27:821–827), while with respect to *Streptococcus mutans* and *Streptococcus sobrinus*, imipenem and the monobactam antibiotics did not show the same mode of action.

Here, both aztreonam and carumonam had the mode of action of bactericidal to *Streptococcus mutans* and *Streptococcus sobrinus*.

Although in the above-described susceptibility tests to the antibiotics, only the two kinds of bacterial strains classified into the serotype c out of *Streptococcus mutans*, and only the two kinds of bacterial strains classified into the serotype d out of *Streptococcus sobrinus* were used, the susceptibilities of bacterial strains classified into the various serotypes to the monobactam antibiotics were studied. The results are shown in Table 3 below.

TABLE 2

Susceptibilities of *Streptococcus mutans* and *Streptococcus sobrinus* to β-lactam antibiotics

| | MIC(µg/mL) | | | |
|---|---|---|---|---|
| | *Streptococcus mutans* | | *Streptococcus sobrinus* | |
| Antibiotic | JC2(c)[a] | 10449(c) | OMZ176(d) | B-13(d) |
| Cephaloridine | 0.025 | 0.025 | 0.025 | 0.025 |
| Cefazoline | 0.25 | 0.25 | 0.25 | 0.50 |
| Cloxacillin | 0.63 | 0.63 | 1.25 | 1.25 |
| Imipenem | 0.125 | 0.125 | 0.031 | 0.016 |
| Aztreonam | 125 | 125 | 2000 | 2000 |
| Carumonam | 125 | 125 | 2000 | 2000 |
| Cephalexin | 1.25 | 1.25 | 1.25 | 1.25 |
| Benzylpenicillin | 0.1 | 0.1 | 0.05 | 0.05 |
| Cefoxitin | 3.13 | 3.13 | 12.5 | 3.13 |

[a]Serotype given in parentheses.

TABLE 3

Susceptibilities of bacterial strains classified into various serotypes of *Streptococcus mutans* and *Streptococcus sobrinus* to monobactam antibiotics

| | | MIC(µg/mL) | |
|---|---|---|---|
| Strain | Serotype | Aztreonam | Carumonam |
| *Streptococcus mutans* | | | |
| PS14 | c | 125 | 125 |
| Ingbritt | c | 125 | 125 |
| LM7 | e | 125 | 125 |
| NUM-Sme1 | e | 125 | 125 |
| OMZ175 | f | 250 | 250 |
| NUM-Smf1 | f | 250 | 250 |
| *Streptococcus sobrinus* | | | |
| NUM-Ssd1 | d | 2000 | 2000 |
| NUM-Ssd2 | d | 2000 | 2000 |

TABLE 3-continued

Susceptibilities of bacterial strains classified into various serotypes of *Streptococcus mutans* and *Streptococcus sobrinus* to monobactam antibiotics

| | | MIC(μg/mL) | |
|---|---|---|---|
| Strain | Serotype | Aztreonam | Carumonam |
| NIDR6715 | g | 2000 | 2000 |
| OMZ65 | g | 2000 | 1000 |

From the results shown in Table 3, the bacterial strains classified into the serotypes c and e of *Streptococcus mutans* had MICs of 125 μg/mL, respectively, in the same as the results shown in Table 2. The bacterial strains classified into the serotype f of *Streptococcus mutans* had MICs of 250 μg/mL, respectively, and had the susceptibilities to aztreonam and carumonam lower than the bacterial strains classified into the serotypes c and e.

The bacterial strains classified into the serotypes d and g of *Streptococcus sobrinus* had MICs in the same as the results shown in Table 2, respectively, except that OMZ65 strain classified into the serotype g had an MIC to carumonam of 1000 μg/mL, it having the susceptibility twice as high as the other bacterial strains.

Also, both aztreonam and carumonam had the mode of action of bactericidal to the bacterial strains of *Streptococcus mutans* and *Streptococcus sobrinus* as shown in Table 3.

From the results shown in Tables 2 and 3, it became clear that the susceptibilities of *Streptococcus sobrinus* to the monobactam antibiotics were significantly lower than those of *Streptococcus mutans*. Therefore, it is understood that *Streptococcus sobrinus* can grow on a medium containing the monobactam antibiotics in such a concentration that *Streptococcus mutans* can not grow, and such a medium allow *Streptococcus sobrinus* alone to grow selectively. Namely, the present inventors have found that by the use of the monobactam antibiotics, *Streptococcus sobrinus* alone can selectively be isolated.

EXAMPLES

Now, the present invention will be specifically described with reference to examples. On the basis of the abovementioned findings, the present inventors produced a trial model of a selective medium for *Streptococcus sobrinus* and evaluated it.

Preparation of Selective Medium

The selective medium for *Streptococcus sobrinus* having the composition shown in Table 4 below (hereinafter this medium will be referred to as MS-SOB medium.) was prepared.

TABLE 4

Composition of Selective Medium for *Streptococcus sobrinus* (MS-SOB medium)

| Component | |
|---|---|
| Mitis Salivarius Medium | 90 g/L |
| Aztreonam | 0.2 g/L |
| Fosfomycin | 0.02 g/L |
| Bacitracin | 20 units/L |
| Sodium Chloride | 20 g/L |

Mitis Salivarius medium (MS medium) in Table 4, manufactured by Difco, which is generally used for isolation of not only mutans streptococci but also the other streptococci, has the following composition.

| Bacto Tryptose | 10 g/L |
|---|---|
| Bacto Proteose Peptone No. 3 | 5 g/L |
| Bacto Proteose Peptone | 5 g/L |
| Bacto Dextrose | 1 g/L |
| Bacto Saccharose | 50 g/L |
| Dipottasium Phosphate | 4 g/L |
| Trypan Blue | 0.075 g/L |
| Bacto Crystal Violet | 0.0008 g/L |
| Bacto Agar | 15 g/L |

However, the base medium used for the selective medium for *Streptococcus sobrinus* of the present invention is not limited to the MS medium, and any media may be used on which only oral streptococci including mutans streptococci can grow.

Although aztreonam is used in the MS-SOB medium as the monobactam antibiotic, the monobactam antibiotic used in the present invention is not limited to aztreonam, and the antibiotics classified into the monobactam antibiotics, for instance, carumonam may be used. Further, the monobactam antibiotics available commercially in Japan at present are only two kinds of aztreonam and carumonam but the monobactam antibiotics used in the present invention are not limited to these two antibiotics. The concentration of the monobactam antibiotic are determined from the results shown in Table 2 and 3 within such a range that *Streptococcus sobrinus* can grow and the other oral streptococci including mutans streptococci can significantly be controlled. The concentration of the monobactam antibiotic is usually within a range of from 0.05 to 0.5 g/L, preferably from 0.1 to 0.3 g/L and particularly preferably 0.2 g/L.

Fosfomycin and bacitracin used here were purchased from Sigma. The mechanisms of action of fosfomycin and bacitracin are inhibitions of pyruvate N-acetylglucosamine-3-o-enol transferase and pyrophosphatase by binding to membrane phospholipids; respectively. Namely, the mechanisms of action thereof are to block from synthesizing cell wall peptide glycan. By the combined use of the monobactam antibiotics with fosfomycin and bacitracin which have the modes of action different from the monobactam antibiotics, it was expected that synergistic effect could be obtained. However, in the present invention, agents such as antibiotics to be added to the medium other than the monobactam antibiotic are not limited to fosfomycin and bacitracin. Fosfomycin is preferably used in a concentration of from 0.05 to 0.5 g/L, and bacitracin is preferably used in a concentration of from 5 to 50 units/L.

Sodium chloride is added to the medium for the purpose of adjusting osmotic pressure and the like, and the concentration thereof in the medium may optionally be determined on the basis of the relationship of the type, concentrations and so on of the other components, and is preferably within a range of from 5 to 40 g/L.

To the selective medium for *Streptococcus sobrinus* of the present invention, additional components capable of increasing the selectivity of *Streptococcus sobrinus* other than the components described in Table 4 above may be added.

The MS medium to which sodium chloride was added was sterilized and the medium was cooled to a temperature of 50° C. Then, the above-mentioned three kinds of antibiotics were added to the medium to prepare the MS-SOB medium.

Performance Evaluation Test of Selectivity to *Streptococcus sobrinus*

By the use of the MS-SOB medium and the MS medium selected as a medium on which oral streptococci including mutans streptococci can grow, the recoveries of *Streptococcus sobrinus* were obtained, to evaluate the performance of selectivity of the MS-SOB medium to *Streptococcus sobrinus*.

The bacterial strains indicated in Table 5 below were incubated anaerobically at 37° C. over night in advance. Ten-fold dilution of the culture solution was prepared by the addition of 0.9 mL of Tris-HCl buffer (0.05 M, pH 7.2) thereto, aliquots of 0.1 mL of the dilution were plated on the test media (MS-SOB and MS), respectively. The plates were incubated anaerobically at a temperature of 37° C. for 3 days, and then, colony forming units (CFU/mL) were counted. The results are shown in Table 5.

TABLE 5

Recoveries of Oral Streptococci and Mutans Streptococci on MS Medium and MS-SOB Medium

| | | Recovery (CFU %) | |
|---|---|---|---|
| Strain | Serotype | MS medium | MS-SOB medium |
| *Streptococcus cricetus* | | | |
| OMZ-61 | a | $1.3 \times 10^7$ | $1.8 \times 10^5$ (13.5) |
| E49 | a | $1.0 \times 10^7$ | 0 (0) |
| *Streptococcus rattus* | | | |
| BHT | b | $1.1 \times 10^8$ | 0 (0) |
| FA1 | b | $2.4 \times 10^8$ | 0 (0) |
| *Streptococcus mutans* | | | |
| JC2 | c | $2.9 \times 10^8$ | 0 (0) |
| NCTC10449 | c | $1.9 \times 10^8$ | 0 (0) |
| LM7 | e | $2.4 \times 10^8$ | 0 (0) |
| NUM-Sme1 | e | $3.0 \times 10^8$ | 0 (0) |
| OMZ175 | f | $1.4 \times 10^8$ | 0 (0) |
| NUM-Smf1 | f | $6.3 \times 10^7$ | 0 (0) |
| *Streptococcus sobrinus* | | | |
| OMZ176 | d | $1.0 \times 10^7$ | $7.0 \times 10^6$ (70.2) |
| B13 | d | $5.8 \times 10^7$ | $4.7 \times 10^7$ (81.3) |
| NUM-Ssd1 | d | $1.4 \times 10^7$ | $1.2 \times 10^7$ (84.8) |
| NIDR6715 | g | $1.5 \times 10^7$ | $1.1 \times 10^7$ (70.7) |
| OMZ65 | g | $2.5 \times 10^7$ | $1.5 \times 10^7$ (60.8) |
| NUM-Ssg1 | g | $1.8 \times 10^8$ | $1.4 \times 10^8$ (76.6) |
| *Streptococcus downeii* | | | |
| NCTC11391 | h | $6.5 \times 10^8$ | $3.9 \times 10^8$ (60.2) |
| *Streptococcus salivarius* | | | |
| ATCC9222 | | $2.0 \times 10^8$ | 0 (0) |
| HHT | | $2.3 \times 10^8$ | 0 (0) |
| *Streptococcus mitis* | | | |
| NCTC3168 | | $9.6 \times 10^7$ | 0 (0) |
| ATCC903 | | $1.2 \times 10^8$ | 0 (0) |
| *Streptococcus sanguis* | | | |
| ATCC10556 | | $4.5 \times 10^8$ | 0 (0) |
| *Streptococcus oralis* | | | |
| ATCC10557 | | $2.4 \times 10^8$ | 0 (0) |
| *Streptococcus gordonii* | | | |
| ATCC10558 | | $9.4 \times 10^7$ | 0 (0) |
| Challis | | $1.1 \times 10^8$ | 0 (0) |
| *Streptococcus anginosus* | | | |
| ATCC9895 | | $8.0 \times 10^7$ | $2.0 \times 10^3$ (0.0025) |
| NCTC10709 | | $3.4 \times 10^8$ | $1.0 \times 10^3$ (0.0003) |

As is apparent from Table 5 above, all the bacterial strains used for the test grew well on the MS medium at a density of from $10^7$ to $10^8$ CFU/mL. On the other hand, the bacterial strains able to grow on the MS-SOB medium were limited only to *Streptococcus cricetus* OMZ-61 strain (recovery: 13.5%) out of the serotype a, all of the bacterial strains classified into the serotypes d and g of *Streptococcus sobrinus* (recovery: 74.1% on the average), *Streptococcus downeii* NCTC11391 strain of the serotype h (recovery: 60.2%), and *Streptococcus anginosus* ATCC9895 strain (recovery: 0.0025%) and NCTC10709 strain (recovery: 0.0003%).

Out of mutans streptococci able to grow on the MS-SOB medium, *Streptococcus cricetus* OMZ-61 strain of the serotype a is a rare bacterial strain detected in the oral cavity. Although *Streptococcus downeii* NCTC11391 strain of the serotype h was found at a high recovery of 60.2%, this bacterial strain has not been detected from human oral cavity up until now. Further, these bacterial strains can be distinguished from *Streptococcus sobrinus* in their colony morphological features. Therefore, it is vanishingly impossible to confuse these bacterial strains and *Streptococcus sobrinus*.

*Streptococcus anginosus* ATCC9895 strain and NCTC10709 strain belonging to the oral streptococci are extremely low in their recoveries, and they have features significantly different from *Streptococcus sobrinus* in their colony morphology. Therefore, even when these bacterial strains inhabit together with *Streptococcus sobrinus*, a person who is not conversant with their colony morphologies can certainly distinguished between *Streptococcus sobrinus* and these bacterial strains.

Out of the tested mutans streptococci, *Streptococcus mutans* which are hardly distinguished from *Streptococcus sobrinus* based on their colony morphologies can not grow on the MS-SOB medium at all, therefore, there is no possibility to confuse *Streptococcus mutans* and *Streptococcus sobrinus*.

From the above-mentioned facts, it is understood that by the use of the MS-SOB medium, *Streptococcus sobrinus* can be isolated selectively.

Confirmation of Selectivity of MS-SOB Medium using Clinical Samples

The selectivity of the MS-SOB medium was confirmed with respect to clinical samples obtained from the dental caries area in human oral cavity.

Sampling area of dental caries was wiped with a cotton roll, and saliva was removed from the sampling area with air blast for a short period of time. Then, sample was taken out from the area of dental caries with a sterilized dental probe. Each sample was taken into a sterilized micro-centrifuging tube containing 1 mL of 50 mM Tris-HCl buffer (pH 7.2). After ultrasonic dispersion, by the use of the same buffer, ten-fold serial dilutions of each sample were prepared, and appropriate dilutions were plated-triplicate on the MS plate medium and the MS-SOB plate medium. These plate media were incubated anaerobically at a temperature of 37° C. for 3 days, and then, recoveries (CFU%) were calculated. The samples containing bacteria in the total number of $1 \times 10^6$ to $10^8$ on the average were used for clinical analysis.

Five colonies per a test subject, which seemed to be *Streptococcus sobrinus* in the light of their colony morphology, were subcultured to confirm the presence of *Streptococcus sobrinus*.

The pure culture strain from each separated strain was identified by 1) the colony morphology; 2) the fermentation pattern using their rapid ID 32 STREP (manufactured by bio Metrieux) or Streptogram (manufactured Wako Pure Chemical Industries Ltd.); and 3) agar gel immunodiffusion method using rabbit antiserum generated against the control strain prepared in our laboratory as mentioned above (Hirasawa, M. et al., 1980, Infect. Immun. 27:697–699; and Igarashi, T. et al., 1996, Oral Microbiol. Immunol. 5:294–298).

The clinical samples were divided into two groups of Group I having the ratio of *Streptococcus sobrinus* in all the streptococci of less than 1%, and Group II having the ratio of not less than 1%, on the basis of the number of existing *Streptococcus sobrinus*. All the samples contained the streptococci in the number of $10^6$ to $10^7$ on the average on the MS plate medium.

By the use of the above-mentioned clinical samples, the recoveries of *Streptococcus sobrinus* were calculated. The results are shown in Table 6 below.

*cus sobrinus* and the other bacteria inhabited together in almost the same quantity. It was difficult to find out *Streptococcus sobrinus* from the sample on the MS plate medium of Group II, which was contaminated by the other bacteria, as was expected.

From the results of Table 6 above, it is understood that by the use of the MS-SOB medium, *Streptococcus sobrinus* can selectively be isolated from clinical dental caries samples.

Study on Bacterial Growth on MS-SOB Medium with Respect to Clinical Dental Caries Sample Sixty human clinical dental caries samples were incubated on the MS-SOB media, and the results of incubation are shown in Table 7 below. Here, all of these 60 samples contained bacteria in the number of $1 \times 10^7$ on the average when measured on the MS plate media.

TABLE 7

Isolation of *Streptococcus sobrinus* on MS-SOB medium from 60 human clinical dental caries samples

| Growth[a] | Number of Samples |
|---|---|
| *Streptococcus sobrinus* pure culture | 14 |
| *Streptococcus sobrinus* plus other bacteria | 4 |
| Other bacteria only | |
| >500 | 0 |
| 10 to 500 | 10 |

TABLE 6

Recoveries of *Streptococcus sobrinus* on MS medium and MS-SOB medium from human dental caries samples

| Group | Percentage of *Streptococcus sobrinus* in all bacteria | Number of samples | MS-SOB medium | | MS medium[a] | |
|---|---|---|---|---|---|---|
| | | | *Streptococcus sobrinus* | Other bacteria | *Streptococcus sobrinus* | Other bacteria |
| I | Less than 1% | 10 | $7.6 \times 10^{3, b}$ ($4 \times 10$ to $6.9 \times 10^4$) | $1.9 \times 10$ ($0$ to $7.0 \times 10$) | N.D.[c] | $6.2 \times 10^6$ ($5.0 \times 10^4$ to $3.0 \times 10^7$) |
| II | Not less than 1% | 8 | $5.4 \times 10^{6, a}$ ($1.8 \times 10^5$ to $3.6 \times 10^7$) | 0 | $5.6 \times 10^6$ ($1.0 \times 10^5$ to $3.7 \times 10^7$) | $2.3 \times 10^7$ ($6.5 \times 10^5$ to $6.6 \times 10^7$) |

[a] Mean number of CFU per mL on the triplicate plates containing 0.1 mL of a $10^{-4}$ or $10^{-5}$ dilution range
[b] Mean number of CFU per mL on the triplicate plates containing 0.1 mL of an undiluted sample or a $10^{-1}$ dilution
[c] N.D.: Not detectable, plates too crowded.
Number given in parenthesis indicates a range of detection.

As is apparent from the results of Table 6 above, in Group I, no *Streptococcus sobrinus* was detected on the crowded MS plate medium. On the other hand, on the MS-SOB medium, even less than 1% of *Streptococcus sobrinus* inhabited among the bacteria of the total number of from $10^6$ to $10^7$ could be detected. When the MS-SOB medium was used, the bacteria other than *Streptococcus sobrinus* were almost totally inhibited. The bacteria other than *Streptococcus sobrinus*, which grew on the MS-SOB medium, formed a small number of colonies or pinpoint colonies.

As for the samples of Group II, the pure strains of *Streptococcus sobrinus* were obtained on the MS-SOB medium, and the other bacteria (contaminants) did not grow on the MS-SOB medium. On the MS medium, *Streptococ- TABLE 7-continued Isolation of *Streptococcus sobrinus* on MS-SOB medium from 60 human clinical dental caries samples

| Growth[a] | Number of Samples |
|---|---|
| <10 | 9 |
| No bacterial growth | 23 |

[a] Mean number of CFU per mL on the triplicate plates containing 0.1 mL of an undiluted sample.

In 14 samples out of the 60 samples, *Streptococcus sobrinus* alone grew, and in 23 samples, no growth of any bacteria was observed.

In 4 samples, growth of *Streptococcus sobrinus* was mainly observed with the small number of colonies (number of colonies: 70 at the maximum) of the other bacteria (contaminants). These other bacteria could morphologically be distinguished from *Streptococcus sobrinus*.

Although growth of the other bacteria alone was observed in 19 samples, these bacteria formed their colonies in the number of less than $5 \times 10^2$ CFU/mL at the maximum. These other bacteria were, of course, morphologically distinguishable from *Streptococcus sobrinus*.

INDUSTRIAL APPLICABILITY

According to the present invention, a method of substantially isolating *Streptococcus sobrinus* alone selectively and a selective medium for *Streptococcus sobrinus*.

According to the present invention, there is no necessity to morphologically distinguish between *Streptococcus mutans* and *Streptococcus sobrinus*, which are closely resemble to each other in their morphologies so that the distinction of these species requires a lot of skill. Therefore, no confusion of these bacterial species could be brought about. Further, no confusion of *Streptococcus sobrinus* with oral streptococci including the mutans streptococci other than *Streptococcus sobrinus* could be brought about, too.

By the use of the selective medium of the present invention, *Streptococcus sobrinus* alone can selectively be isolated among oral streptococci including mutans streptococci and can be incubated, thereby it being possible to clarify the exact aspect of the presence of *Streptococcus sobrinus* in clinical dental caries samples.

If the aspect of the presence of *Streptococcus sobrinus* can be exactly gotten hold of, it becomes possible to clarify the significance and role of *Streptococcus sobrinus* in caries risk, which has been discussed in the art.

Furthermore, in the future, the distribution of *Streptococcus sobrinus* in oral cavity will be investigated and be able to be used for diagnosis of the caries risk of a patient.

The invention claimed is:

1. A method of substantially isolating *Streptococcus sobrinus* alone comprising
    adding a monobactam antibiotic to a medium on which only oral streptococci including mutans streptococci can grow;
    culturing a sample of the medium; and
    isolating *Streptococcus sobrinus* from the medium.

2. The method according to claim 1, wherein the medium is Mitis Salivarius Agar.

3. The method according to claim 1, wherein the monobactam antibiotic is aztreonam (AZT) or carumonam (CRMN).

4. The method according to claim 3, wherein the monobactam antibiotic is aztreonam (AZT).

5. The method according to claim 1, wherein the monobactam antibiotic is added to the medium in a concentration of from 0.05 to 0.5 g/L.

6. The method according to claim 1, wherein the medium comprises fosfomycin, bacitracin and sodium chloride.

7. The method according to claim 1, which comprises:

| | |
|---|---|
| Mitis Salivarius Medium | 90 g/L |
| Aztreonam | 0.05 0.5 g/L |
| Fosfomycin | 0.05–0.5 g/L |
| Bacitracin | 5–50 units/L |
| Sodium Chloride | 5–40 g/L. |

8. A selective medium for *Streptococcus sobrinus* prepared by adding a monobactam antibiotic to a medium on which only oral streptococci including mutans streptococci can grow.

9. The selective medium for *Streptococcus sobrinus* according to claim 8, wherein the medium on which only oral streptococci can grow is Mitis Salivarius Agar.

10. The selective medium for *Streptococcus sobrinus* according to claim 9, wherein the monobactam antibiotic is aztreonam (AZT) or carumonam (CRMN).

11. The selective medium for *Streptococcus sobrinus* according to claim 10, wherein the monobactam antibiotic is aztreonam (AZT).

12. The selective medium for *Streptococcus sobrinus* according to claim 8, wherein the monobactam antibiotic is aztreonam (AZT) or carumonam (CRMN).

13. The selective medium for *Streptococcus sobrinus* according to claim 12, wherein the monobactam antibiotic is aztreonam (AZT).

14. The selective medium for *Streptococcus sobrinus* according to claim 8, wherein the monobactam antibiotic is present in the medium in a concentration of from 0.05 to 0.5 g/L.

15. The selective medium for *Streptococcus sobrinus* according to claim 8, wherein the selective medium further comprises fosfomycin and/or bacitracin.

16. The selective medium for *Streptococcus sobrinus* according to claim 8, which comprises:

| | |
|---|---|
| Mitis Salivarius Medium | 90 g/L |
| Aztreonam | 0.05–0.5 g/L |
| Fosfomycin | 0.05–0.5 g/L |
| Bacitracin | 5–50 units/L |
| Sodium Chloride | 5–40 g/L. |

* * * * *